(12) United States Patent
Bedate et al.

(10) Patent No.: US 7,189,399 B2
(45) Date of Patent: *Mar. 13, 2007

(54) CHIMERIC GENE FORMED OF THE DNA SEQUENCES THAT ENCODE THE ANTIGENIC DETERMINANTS OF FOUR PROTEINS OF L. INFANTUM, USEFUL FOR SEROLOGIC DIAGNOSIS OF CANINE LEISHMANIOSIS AND PROTEIN OBTAINED

(75) Inventors: Carlos Alonso Bedate, Madrid (ES); Jose Maria Requena Rolania, Madrid (ES); Manuel Soto Alvarez, Madrid (ES)

(73) Assignee: Laboratories Leti, S.L. Unipersonal, Madrid (IT)

( * ) Notice: Subject to any disclaimer, the term of this patent is extended or adjusted under 35 U.S.C. 154(b) by 0 days.

This patent is subject to a terminal disclaimer.

(21) Appl. No.: 11/168,874

(22) Filed: Jun. 29, 2005

(65) Prior Publication Data

US 2005/0287176 A1    Dec. 29, 2005

Related U.S. Application Data

(60) Division of application No. 10/337,312, filed on Jan. 7, 2003, now Pat. No. 6,929,795, which is a division of application No. 09/788,345, filed on Feb. 21, 2001, now Pat. No. 6,525,186, which is a continuation-in-part of application No. 09/219,306, filed on Dec. 23, 1998, now abandoned.

(51) Int. Cl.
*A61K 39/00*    (2006.01)
*A61K 39/002*    (2006.01)
*A61K 39/38*    (2006.01)

(52) U.S. Cl. .............................. 424/184.1; 424/192.1; 424/269.1

(58) Field of Classification Search ............. 424/184.1, 424/192.1, 269.1
See application file for complete search history.

(56) References Cited

OTHER PUBLICATIONS

Ravindran et al (Current Molecule Medicine vol. 4, pp. 697-709, 2004).*
Soto et al., GenEmbl Accession No. X68015: L. infantum LiP gene for acidic ribosomal protein LiP (Nov. 1993).
Soto et al. *J. Clin. Microbiol* 1998, 36:58-63.
Plotkin et al (Vaccines, WB Saunders Company, 1988, pp. 571).

* cited by examiner

*Primary Examiner*—Mark Navarro
(74) *Attorney, Agent, or Firm*—Browdy and Neimark, PLLC (57) ABSTRACT

Chimeric gene formed by the DNA sequences that encode the antigenic determinants of four proteins of *L. infantum*, useful for the serological diagnosis of canine Leishmaniosis and protein obtained, that consists of the prior employment of a cloning strategy. The patent describes the intermediate products generated during the process. A clone is achieved expressed in the protein rLiPO-Ct-Q (pPQI). To this initial vector, by means of the use of suitable restriction targets, DNA fragments are sequentially added that are encoded in other proteins and after each cloning step the correct orientation of each one of the inserts reduces the size of the expression products, the complete nucleotide sequence of the final pPQV clone being determined. A polypeptide is obtained with a molecular mass of 38 kD and with an isoelectric point of 7.37.

2 Claims, 6 Drawing Sheets

| | | |
|---|---|---|
| MBP | IEGRPLATPRSAKKAVRKSGSKSAKCGLIFPVGRVGGMMRRGQYARRIGA | 50 |
| | SGAPRISEFSVKAAAQSGKKRCRLNPRTVMLAARHDDDIGTLLKNVTLSHSGVV | 104 |
| | PNISKAMAKKKGGKKGKATPSAPEFGSSRPMSTKYLAAYALASLSKASPSQAD | 157 |
| | VEAICKAVHIDVDQATLAFVMESVTGRDVATLIAEGAAKMSAMPAASSGAAAGV | 211 |
| | TASAAGDAAPAAAAAKKDEPEEEADDDMGPSRVDPMQYLAAYALVALSGKTPSK | 265 |
| | ADVQAVLKAAGVAVDASRVDAVFQEVEGKSFDALVAEGRTKLVGSGSAAPAGAV | 319 |
| | STAGAGAGAVAEAKKEEPEEEEADDDMGPVDLQPAAAAPAAPSAAAKEEPEESD | 373 |
| | EDDFGMGGLF | |

SEQUENCE LISTING

<160> NUMBER OF SEQ ID NOS: 12

<210> SEQ ID NO 1
<211> LENGTH: 27
<212> TYPE: DNA
<213> ORGANISM: Artificial Sequence
<220> FEATURE:

-continued

<223> OTHER INFORMATION: synthetic

<400> SEQUENCE: 1
cctttagcta ctcctcgcag cgccaag　　　　　　　　　　　　　　　　　27

<210> SEQ ID NO 2
<211> LENGTH: 27
<212> TYPE: DNA
<213> ORGANISM: Artificial Sequence
<220> FEATURE:
<223> OTHER INFORMATION: synthetic

<400> SEQUENCE: 2 cctggggcg ccagaggcac cgatgcg　　　　　　　　　　　　　　　　　27

<210> SEQ ID NO 3
<211> LENGTH: 26
<212> TYPE: DNA
<213> ORGANISM: Artificial Sequence
<220> FEATURE:
<223> OTHER INFORMATION: synthetic

<400> SEQUENCE: 3
gaattctccg taaggcggcc gcgcag　　　　　　　　　　　　　　　　　26

<210> SEQ ID NO 4
<211> LENGTH: 30
<212> TYPE: DNA
<213> ORGANISM: Artificial Sequence
<220> FEATURE:
<223> OTHER INFORMATION: synthetic

<400> SEQUENCE: 4
gaattcgggc gcgctcggtg tcgccttgcc　　　　　　　　　　　　　　　　30

<210> SEQ ID NO 5
<211> LENGTH: 30
<212> TYPE: DNA
<213> ORGANISM: Artificial Sequence
<220> FEATURE:
<223> OTHER INFORMATION: synthetic

<400> SEQUENCE: 5
gtcgacccca tgcagtacct cgccgcgtac　　　　　　　　　　　　　　　　30

<210> SEQ ID NO 6
<211> LENGTH: 30
<212> TYPE: DNA
<213> ORGANISM: Artificial Sequence
<220> FEATURE:
<223> OTHER INFORMATION: synthetic

<400> SEQUENCE: 6
gtcgacgggg cccatgtcat catcggcctc　　　　　　　　　　　　　　　　30

<210> SEQ ID NO 7
<211> LENGTH: 32
<212> TYPE: DNA
<213> ORGANISM: Artificial Sequence
<220> FEATURE:
<223> OTHER INFORMATION: synthetic

<400> SEQUENCE: 7
tctagacccg ccatgtcgtc gtcttcctcg cc　　　　　　　　　　　　　　32

<210> SEQ ID NO 8
<211> LENGTH: 29
<212> TYPE: DNA
<213> ORGANISM: Artificial Sequence
<220> FEATURE:
<223> OTHER INFORMATION: synthetic

<400> SEQUENCE: 8
tctagagggg ccatgtcgtc gtcggcctc                                29

<210> SEQ ID NO 9
<211> LENGTH: 30
<212> TYPE: DNA
<213> ORGANISM: Artificial Sequence
<220> FEATURE:
<223> OTHER INFORMATION: synthetic

<400> SEQUENCE: 9
ctgcagcccg ccgctgccgc gccggccgcc                               30

<210> SEQ ID NO 10
<211> LENGTH: 383
<212> TYPE: PRT
<213> ORGANISM: Artificial Sequence
<220> FEATURE:
<223> OTHER INFORMATION: chimeric

<400> SEQUENCE: 10

```
Ile Glu Gly Arg Pro Leu Ala Thr Pro Arg Ser Ala Lys Lys Ala Val
  1               5                  10                  15

Arg Lys Ser Gly Ser Lys Ser Ala Lys Cys Gly Leu Ile Phe Pro Val
             20                  25                  30

Gly Arg Val Gly Gly Met Met Arg Arg Gly Gln Tyr Ala Arg Arg Ile
         35                  40                  45

Gly Ala Ser Gly Ala Pro Arg Ile Ser Glu Phe Ser Val Lys Ala Ala
     50                  55                  60

Ala Gln Ser Gly Lys Lys Arg Cys Arg Leu Asn Pro Arg Thr Val Met
 65                  70                  75                  80

Leu Ala Ala Arg His Asp Asp Ile Gly Thr Leu Leu Lys Asn Val
                 85                  90                  95

Thr Leu Ser His Ser Gly Val Val Pro Asn Ile Ser Lys Ala Met Ala
                100                 105                 110

Lys Lys Lys Gly Gly Lys Lys Gly Lys Ala Thr Pro Ser Ala Pro Glu
            115                 120                 125

Phe Gly Ser Ser Arg Pro Met Ser Thr Lys Tyr Leu Ala Ala Tyr Ala
        130                 135                 140

Leu Ala Ser Leu Ser Lys Ala Ser Pro Ser Gln Ala Asp Val Glu Ala
145                 150                 155                 160

Ile Cys Lys Ala Val His Ile Asp Val Asp Gln Ala Thr Leu Ala Phe
                165                 170                 175

Val Met Glu Ser Val Thr Gly Arg Asp Val Ala Thr Leu Ile Ala Glu
            180                 185                 190

Gly Ala Ala Lys Met Ser Ala Met Pro Ala Ala Ser Ser Gly Ala Ala
        195                 200                 205

Ala Gly Val Thr Ala Ser Ala Ala Gly Asp Ala Ala Pro Ala Ala Ala
    210                 215                 220

Ala Ala Lys Lys Asp Glu Pro Glu Glu Ala Asp Asp Met Gly
225                 230                 235                 240

Pro Ser Arg Val Asp Pro Met Gln Tyr Leu Ala Ala Tyr Ala Leu Val
```

245                  250                   255
Ala Leu Ser Gly Lys Thr Pro Ser Lys Ala Asp Val Gln Ala Val Leu
            260                 265                 270

Lys Ala Ala Gly Val Ala Val Asp Ala Ser Arg Val Asp Ala Val Phe
            275                 280                 285

Gln Glu Val Glu Gly Lys Ser Phe Asp Ala Leu Val Ala Glu Gly Arg
    290                 295                 300

Thr Lys Leu Val Gly Ser Gly Ser Ala Ala Pro Ala Gly Ala Val Ser
305                 310                 315                 320

Thr Ala Gly Ala Gly Ala Gly Val Ala Glu Ala Lys Lys Glu Glu
                325                 330                 335

Pro Glu Glu Glu Ala Asp Asp Met Gly Pro Val Asp Leu Gln
            340                 345                 350

Pro Ala Ala Ala Pro Ala Ala Pro Ser Ala Ala Lys Glu Glu
            355                 360                 365

Pro Glu Glu Ser Asp Glu Asp Asp Phe Gly Met Gly Gly Leu Phe
    370                 375                 380

<210> SEQ ID NO 11
<211> LENGTH: 1436
<212> TYPE: DNA
<213> ORGANISM: Artificial Sequence
<220> FEATURE:
<223> OTHER INFORMATION: recombinant sequence from vectors pQ31 and pMal
<220> FEATURE:
<221> NAME/KEY: CDS
<222> LOCATION: (1)..(1236)
<223> OTHER INFORMATION:

<400> SEQUENCE: 11 atg aga gga tct cac cac cac cac cac cac acg gat ccg cat gcg agc     48
Met Arg Gly Ser His His His His His His Thr Asp Pro His Ala Ser
1               5                   10                  15 tcg aac aac aac aac aat aac aat aac aac aac ctc ggg atc gag gga     96
Ser Asn Asn Asn Asn Asn Asn Asn Asn Asn Asn Leu Gly Ile Glu Gly
                20                  25                  30 agg cct tta gct act cct cgc agc gcc aag aag gcc gtc cgc aag agc    144
Arg Pro Leu Ala Thr Pro Arg Ser Ala Lys Lys Ala Val Arg Lys Ser
            35                  40                  45 ggc tcc aag tcc gcg aaa tgt ggt ctg atc ttc ccg gtg ggc cgc gtc    192
Gly Ser Lys Ser Ala Lys Cys Gly Leu Ile Phe Pro Val Gly Arg Val
    50                  55                  60 ggc ggg atg atg cgc cgc ggc cag tac gct cgc cgc atc ggt gcc tct    240
Gly Gly Met Met Arg Arg Gly Gln Tyr Ala Arg Arg Ile Gly Ala Ser
65                  70                  75                  80 ggc gcc ccc agg att tca gaa ttc tcc gtg aag gcg gcc gcg cag agc    288
Gly Ala Pro Arg Ile Ser Glu Phe Ser Val Lys Ala Ala Ala Gln Ser
                85                  90                  95 ggg aag aag cgg tgc cgc ctg aac ccg cgc acc gtg atg ctg gcc gcg    336
Gly Lys Lys Arg Cys Arg Leu Asn Pro Arg Thr Val Met Leu Ala Ala
            100                 105                 110 cgc cac gac gac gac atc ggc acg ctt ctg aag aac gtg acc ttg tct    384
Arg His Asp Asp Asp Ile Gly Thr Leu Leu Lys Asn Val Thr Leu Ser
        115                 120                 125 cac agc ggc gtt gtg ccg aac atc agc aag gcg atg gca aag aag aag    432
His Ser Gly Val Val Pro Asn Ile Ser Lys Ala Met Ala Lys Lys Lys
    130                 135                 140 ggc ggc aag aag ggc aag gcg aca ccg agc gcg ccc gaa ttc gga tcc    480
Gly Gly Lys Lys Gly Lys Ala Thr Pro Ser Ala Pro Glu Phe Gly Ser
145                 150                 155                 160

```
tct aga ccc atg tcc acc aag tac ctc gcc gcg tac gct ctg gcc tcc      528
Ser Arg Pro Met Ser Thr Lys Tyr Leu Ala Ala Tyr Ala Leu Ala Ser
            165                 170                 175 ctg agc aag gcg tcc ccg tct cag gcg gac gtg gag gct atc tgc aag      576
Leu Ser Lys Ala Ser Pro Ser Gln Ala Asp Val Glu Ala Ile Cys Lys
        180                 185                 190 gcc gtc cac atc gac gtc gac cag gcc acc ctc gcc ttt gtg atg gag      624
Ala Val His Ile Asp Val Asp Gln Ala Thr Leu Ala Phe Val Met Glu
    195                 200                 205 agc gtt acg gga cgc gac gtg gcc acc ctg atc gcg gag ggc gcc gcg      672
Ser Val Thr Gly Arg Asp Val Ala Thr Leu Ile Ala Glu Gly Ala Ala
210                 215                 220 aag atg agc gcg atg ccg gcg gcc agc tct ggt gcc gct gct ggc gtc      720
Lys Met Ser Ala Met Pro Ala Ala Ser Ser Gly Ala Ala Ala Gly Val
225                 230                 235                 240 act gct tcc gct gcg ggt gat gcg gct ccg gct gcc gcc gcc gcg aag      768
Thr Ala Ser Ala Ala Gly Asp Ala Ala Pro Ala Ala Ala Ala Ala Lys
                245                 250                 255 aag gac gag ccc gag gag gag gcc gac gac gac atg ggc ccc tct aga      816
Lys Asp Glu Pro Glu Glu Glu Ala Asp Asp Asp Met Gly Pro Ser Arg
            260                 265                 270 gtc gac ccc atg cag tac ctc gcc gcg tac gcc ctc gtg gcg ctg tct      864
Val Asp Pro Met Gln Tyr Leu Ala Ala Tyr Ala Leu Val Ala Leu Ser
        275                 280                 285 ggc aag acg ccg tcg aag gcg gac gtt cag gct gtc ctg aag gcc gcc      912
Gly Lys Thr Pro Ser Lys Ala Asp Val Gln Ala Val Leu Lys Ala Ala
    290                 295                 300 ggc gtt gcc gtg gat gcc tcc cgc gtg gat gcc gtc ttc cag gag gtg      960
Gly Val Ala Val Asp Ala Ser Arg Val Asp Ala Val Phe Gln Glu Val
305                 310                 315                 320 gag ggc aag agc ttc gat gcg ctg gtg gcc gag ggc cgc acg aag ctg     1008
Glu Gly Lys Ser Phe Asp Ala Leu Val Ala Glu Gly Arg Thr Lys Leu
                325                 330                 335 gtg ggc tct ggc tct gcc gct cct gct ggc gct gtc tcc act gct ggt     1056
Val Gly Ser Gly Ser Ala Ala Pro Ala Gly Ala Val Ser Thr Ala Gly
            340                 345                 350 gcc ggc gct ggc gcg gtg gcc gag gcg aag aag gag gag ccc gag gag     1104
Ala Gly Ala Gly Ala Val Ala Glu Ala Lys Lys Glu Glu Pro Glu Glu
        355                 360                 365 gag gag gcc gat gat gac atg ggc ccc gtc gac ctg cag ccc gcc gct     1152
Glu Glu Ala Asp Asp Asp Met Gly Pro Val Asp Leu Gln Pro Ala Ala
    370                 375                 380 gcc gcg ccg gcc gcc cct agc gcc gct gcc aag gag gag ccg gag gag     1200
Ala Ala Pro Ala Ala Pro Ser Ala Ala Ala Lys Glu Glu Pro Glu Glu
385                 390                 395                 400 agc gac gag gac gac ttc ggc atg ggc ggt ctc ttc taagcgactc          1246
Ser Asp Glu Asp Asp Phe Gly Met Gly Gly Leu Phe
                405                 410 gccatctctt agcctccttg tggtgcgctt gaggtgctct cgctctgctt ctccttgcag   1306
tgttggctga ctctggcggg tatgtgccgt cgcattacac ccacctctcc caccccttg    1366 ccctacgcgc tcgcatgcgc aatccgtgaa tcatcgaggg aagtctctct gggtggcagt  1426
gggtaagctt                                                          1436

<210> SEQ ID NO 12
<211> LENGTH: 412
<212> TYPE: PRT
<213> ORGANISM: Artificial Sequence
<220> FEATURE:
```

<223> OTHER INFORMATION: recombinant sequence from vectors pQ31 and pMal

<400> SEQUENCE: 12

```
Met Arg Gly Ser His His His His His His Thr Asp Pro His Ala Ser
1               5                   10                  15

Ser Asn Asn Asn Asn Asn Asn Asn Asn Asn Leu Gly Ile Glu Gly
            20                  25                  30

Arg Pro Leu Ala Thr Pro Arg Ser Ala Lys Ala Val Arg Lys Ser
            35                  40                  45

Gly Ser Lys Ser Ala Lys Cys Gly Leu Ile Phe Pro Val Gly Arg Val
    50                  55                  60

Gly Gly Met Met Arg Arg Gly Gln Tyr Ala Arg Arg Ile Gly Ala Ser
65                  70                  75                  80

Gly Ala Pro Arg Ile Ser Glu Phe Ser Val Lys Ala Ala Gln Ser
                85                  90                  95

Gly Lys Lys Arg Cys Arg Leu Asn Pro Arg Thr Val Met Leu Ala Ala
            100                 105                 110

Arg His Asp Asp Asp Ile Gly Thr Leu Leu Lys Asn Val Thr Leu Ser
    115                 120                 125

His Ser Gly Val Val Pro Asn Ile Ser Lys Ala Met Ala Lys Lys Lys
130                 135                 140

Gly Gly Lys Lys Gly Lys Ala Thr Pro Ser Ala Pro Glu Phe Gly Ser
145                 150                 155                 160

Ser Arg Pro Met Ser Thr Lys Tyr Leu Ala Ala Tyr Ala Leu Ala Ser
                165                 170                 175

Leu Ser Lys Ala Ser Pro Ser Gln Ala Asp Val Glu Ala Ile Cys Lys
            180                 185                 190

Ala Val His Ile Asp Val Asp Gln Ala Thr Leu Ala Phe Val Met Glu
        195                 200                 205

Ser Val Thr Gly Arg Asp Val Ala Thr Leu Ile Ala Glu Gly Ala Ala
    210                 215                 220

Lys Met Ser Ala Met Pro Ala Ser Ser Gly Ala Ala Ala Gly Val
225                 230                 235                 240

Thr Ala Ser Ala Ala Gly Asp Ala Ala Pro Ala Ala Ala Ala Lys
                245                 250                 255

Lys Asp Glu Pro Glu Glu Ala Asp Asp Met Gly Pro Ser Arg
            260                 265                 270

Val Asp Pro Met Gln Tyr Leu Ala Ala Tyr Ala Leu Val Ala Leu Ser
                275                 280                 285

Gly Lys Thr Pro Ser Lys Ala Asp Val Gln Ala Val Leu Lys Ala Ala
    290                 295                 300

Gly Val Ala Val Asp Ala Ser Arg Val Asp Ala Val Phe Gln Glu Val
305                 310                 315                 320

Glu Gly Lys Ser Phe Asp Ala Leu Val Ala Glu Gly Arg Thr Lys Leu
                325                 330                 335

Val Gly Ser Gly Ser Ala Ala Pro Ala Gly Ala Val Ser Thr Ala Gly
            340                 345                 350

Ala Gly Ala Gly Ala Val Ala Glu Ala Lys Lys Glu Glu Pro Glu Glu
        355                 360                 365

Glu Glu Ala Asp Asp Met Gly Pro Val Asp Leu Gln Pro Ala Ala
    370                 375                 380

Ala Ala Pro Ala Ala Pro Ser Ala Ala Ala Lys Glu Glu Pro Glu Glu
385                 390                 395                 400
```

-continued

```
Ser Asp Glu Asp Asp Phe Gly Met Gly Gly Leu Phe
                405                 410
```

CHIMERIC GENE FORMED OF THE DNA SEQUENCES THAT ENCODE THE ANTIGENIC DETERMINANTS OF FOUR PROTEINS OF L. INFANTUM, USEFUL FOR SEROLOGIC DIAGNOSIS OF CANINE LEISHMANIOSIS AND PROTEIN OBTAINED

CROSS-REFERENCE TO RELATED APPLICATIONS

This application is a divisional of application Ser. No. 10/337,312, filed Jan. 7, 2003, now U.S. Pat. No. 6,929,795 which is a divisional of application Ser. No. 09/788,345, filed Feb. 21, 2001, now issued as U.S. Pat. No. 6,525,186, which is a continuation-in-part of application Ser. No. 09/219,306, filed Dec. 23, 1998, now abandoned. The entire contents of Ser. No. 09/219,306 and Ser. No. 09/788,345 are incorporated herein entirely by reference.

OBJECT OF THE INVENTION

The present specification relates to an application for an Invention Patent, regarding a chimeric gene formed of the DNA sequences that encode the antigenic determinants of four proteins of *L. infantum*, useful for serologic diagnosis of canine leishmaniosis and protein obtained. The obvious purpose of this lies in using the protein obtained from the chimeric gene to perform an early diagnosis of canine leishmaniosis, that can be present in the body of a patient. This patient does not have to be a dog but can also be a human being who suffers from diseases that involve immuno-depression. This achieves an accurate diagnostic that avoids current diagnostic methods. These, in view of the fact that the antibodies present in animal and human serum to be analysed contain a large quantity of proteins can produce cross reactions, and can therefore give positive results when there is no real infection. Therefore existing types of analysis can give rise to uncontrolled false positive readings.

To summarise, with a view to minimising these problems, a chimeric gene will be produced that encodes a protein called MSPQ consisting of a chimeric product originating from an "in vitro" synthesis of a chimeric gene constructed "ad hoc", which contains five of the antigenic determinants of four different proteins. The product is configured as a highly sensitive and specific for the diagnosis of canine Leishmaniosis.

FIELD OF THE INVENTION

This invention is of utility within the industry dedicated to the manufacture of pharmaceutical products in general.

BACKGROUND OF THE INVENTION

The parasitic protozoa of the *Leishmania* genus are the aetiological agents that cause Leishmaniosis, a range of diseases that have a world-wide distribution and that are characterised in that they give rise to a wide variety of clinical symptoms.

The main forms of Leishmaniosis are zoonotic in nature and humans are considered as secondary hosts.

The species denoted *L. infantum*, widely distributed throughout many Mediterranean areas is the cause of visceral Leishmaniosis (LV) in humans and dogs.

In fact, dogs infected with *L. infantum* are the main animal reserve of this parasite, particularly during the long incubation period before the clinical symptoms can be observed.

The epidemiological data indicate that there is a direct correlation between the prevalence of canine Leishmaniosis and the transmission of the parasite to humans. For this reason, it is crucial to detect the disease or infection early on in campaigns undertaken to control the spread of the disease.

The parasite is transmitted to the host vertebrate as a flagellate promastigote, by means of a bite of a fly of the family "Phlebotominae", and the parasite enter the cells of the mononuclear phages where they differentiate and reproduce as amastigotes, within the phago-lisosomal structure.

The infected cells gather in certain tissues, mainly spleen, liver and lymph nodes. It is estimated that around 15 million people are infected with Leishmaniosis, and every year in the world 500,000 new clinical cases appear in the world, mainly in the underdeveloped and developing world.

In the south-western countries of Europe, Visceral Leishmaniosis (VL), is a zoonotic disease caused by the L. Infantum species, as was mentioned earlier. Recent data derived from epidemiological studies indicate that there is an alarming incidence of this infection.

In Italy the reported data for incidence of VL ranges from 14.4% to 37% according to the region.

In Portugal, more particularly in the area around Lisbon, seropositive rates of 8.4% have been found and in the region of the French Maritime Alps different centres of prevalence have been found that vary between 3.2% and 17.1%.

In Spain, the prevalence of Leishmaniosis depends on the zone being studied. In Catalonia an average incidence rate of 9.3% has been observed although in some hot-spots a prevalence of infected dogs of up to 18% has been found.

On the Island of Mallorca, the incidence rate is 14%, and other rates that have been found are: 2.4% in Murcia, 8.8% in Granada, from 10 to 15% in Salamanca, 5.25% in the province of Madrid, and 14% in Caceres.

Although the number of cases of VL in humans caused by *L. infantum* can be considered relatively low, the high percentage of patients with immuno-depression that become infected by *Leishmania* could be related to the high level of this illness in dogs.

In fact, in the South of Europe, 50% of adults that are infected by Leishmaniosis are also patients infected by the HIV virus. On the other hand, according to these data of *Leishmania*-HIV co-infection, it has been estimated that the level of infection (by parasites) can be one or two orders of magnitude higher than this figure due to the existence of a large number of undetected infections.

A common characteristic of the different types of *Leishmania* infection is that it induces a strong humoral response in the host. Therefore, diagnostic methods based on serological techniques are currently the most widely used.

It has been described that these antibodies are detected even during the asymptomatic phase of the disease in natural and experimental infections.

The sensitivity and specificity of these methods depends on the type, source and purity of the antigen used. In immunological processes that are currently commercialised, complete promastigotes and preparations more or less prepared from these are used as a source of antigen. This method normally leads to cross-reactions with serum from patients suffering from leprosy, tuberculosis, African tripanosomiasis, Chagas disease, malaria and other parasitosis.

The sensitivity and specificity of the serologic methods depend on the type, source and purity of the employed antigen. During the last years a great number of *Leishmania* antigens have been characterised, some of them can be considered as proteins specific to the parasite.

Among these proteins specific to the parasite, the surface protease GP63, the surface glycoprotein gp46 and the lipo-phosphoglicane associated KMP-11 protein deserve a mention.

An additional group of *Leishmania* antigens are formed of evolutionarily conserved proteins, such as kinesine, thermal shock proteins, actin and tubulin.

As part of a strategy to develop a specific serological diagnostic system for Leishmaniosis canine, a laboratory based project has been undertaken to identify the antigens of *L. infantum*, by means of a immuno-detection search of an expression library for genes of *L. infantum* using dog serum with active visceral Leishmaniosis.

It has been observed that most of the antigens isolated by this method belong to the family of proteins conserved during the course of evolution. The identification of the B epitopes of these antigens indicate, however, that in all cases the antigenic determinants were localised in regions that were not well conserved.

In particular, the acidic ribosomal proteins LiP2 a and LiP2b are recognised by more than 80% of the VL serums.

It has been confirmed that these proteins contain disease specific antigenic determinants, and that the recombinant proteins LiP2a and LiP2b, from which a fragment had been removed, could be used as a specific instrument able to distinguish between VL and Chages disease.

It has also been shown that the PO ribosomal protein of *L. infantum*, very highly conserved on the evolutionary scale, is recognised by a high percentage of VL dog serums. Furthermore, the antigenic determinants are found exclusively on the C-terminus of the protein, that is to say, in the region that has been poorly conserved during the course of evolution.

It has been observed that in 78% of the VL dog serums, antigens against H2A protein are also present, and it has been confirmed that despite the sequence identity in all the H2A proteins among eukaryotic organisms, the humoral response to this protein in VL serums is particularly provoked by determinants specific to the *Leishmania* protein H2A.

The antigenic determinants recognised by the VL dog serums are found at both termini of the H2A protein.

The obvious solution to the problem currently encountered in this art would be to have an invention that would allow the assembly of a synthetic chimeric gene that contained the DNA regions encoding the antigenic determinants specific to the proteins LiP2a, LiP2b, LiPO, and H2A, with a view to constructing a protein rich in antigenic determinants.

However, as far as the applicant is aware, there is currently no invention that contains the characteristics described as ideal, with a view to reaching the desired aim. This aim is the construction of a protein rich in antigenic determinants, arising from the assembly of a chimeric synthetic gene, that contains the DNA regions encoding the antigenic determinants specific to the aforementioned proteins.

DESCRIPTION OF THE INVENTION

In a first aspect, the invention relates to a chimeric gene formed by the DNA sequences that encode antigenic determinants of four proteins of *L. infantum*, useful for the serum diagnosis of canine Leishmaniosis.

In a further aspect, the invention relates to a protein encoded by said chimeric gene, containing one or more of the antigenic determinants of four proteins of *L. infantum* encoded by the chimeric gene.

The invention further relates to a diagnostic method for determining the presence of canine Leishmaniosis in a human being or an animal, in particular a dog, and/or in samples of biological fluids derived from humans or animals, such as a blood sample. In this diagnostic method, the chimeric gene of the invention or the protein encoded by it can be used. Alternatively, in the diagnostic method, a nucleic acid probe sequences specific for the chimeric gene of the invention, or a part thereof, can be used, i.e. to establish the presence of canine Leishmaniosis in a patient or a sample.

Also, in the diagnostic method, antibodies against the protein encoded by the chimeric gene of the invention, or a antigenic part thereof such as an epitope, can be used.

The invention further relates to assays or other qualitative or quantitative methods for determining the presence of canine Leishmaniosis in a human being or an animal, in particular a dog, and/or in samples of biological fluids derived from humans or animals, such as a blood sample. Such assays can use the chimeric gene of the invention, the protein encoded by it, probes specific for the chimeric gene or part thereof, and/or antibodies directed to the protein encoded by the chimeric gene of the invention, or any antigenic part thereof. Such assays can further be carried out in a manner known per se, for instance for probe-hybridization assays or immunoassays.

In a further aspect, the invention relates to diagnostic kits, at least comprising either a chimeric gene of the invention, a protein encoded by said chimeric gene, a probe specific for the chimeric gene of the invention, or an antibody directed to the protein of the invention. The kits can further contain all components for diagnostic kits and/or diagnostic assays known per se.

It should be noted that when herein, reference is made to the chimeric gene of the invention, this term also encompasses nucleic acid sequences that can hybridize with the sequence mentioned below under moderate or stringent hybridizing conditions.

In this context, heterologous hybridisation conditions can be as follows: hybridisation in 6×SSC (20×SSC per 1000 ml:175.3 g NaCl, 107.1 g sodium citrate.$5H_2O$, pH 7.0), 0.1% SDS, 0.05% sodium pyrophosphate, 5* Denhardt's solution (100× Denhardt's solution per 500 ml:10 g Ficoll-400, 10 g polyvinyl-pyrrolidone, 10 g Bovine Serum Albumin (Pentax Fraction V)) and 20 ig/ml denatured herring sperm DNA at 56° C. for 18–24 hrs followed by two 30 min. washes in 5×SSC, 0.1% SDS at 56° C. and two 30 min. washes in 2×SSC, 0.1% SDS at 56° C.

For instance, sequences that can hybridize with the sequence mentioned below include mutant DNA sequences which encode proteins with the same biological function as the protein encoded by the sequence mentioned hereinbelow. Such mutant sequences can comprise one or more nucleotide deletions, substitutions and/or additions to the sequence mentioned below. Preferably, the mutant sequences still have at least 50%, more preferably at least 70%, even more preferably more than 90% nucleotide homology with the sequence given hereinbelow.

The term chimeric gene as used herein also encompasses nucleic acid sequences that comprise one or more parts of the sequence mentioned hereinbelow. Preferably, such sequences comprise at least 10%, more preferably at least 30%, more preferably at least 50% of the nucleotide sequence given hereinbelow. Such sequences may comprise a contiguous fragment of the sequence mentioned hereinbelow, or two or more fragments of the sequence given below that have been combined in and/or incorporated into a single DNA sequence.

It should be noted that when herein, reference is made to a protein encoded by the chimeric gene of the invention, this term also includes mutant proteins that still essentially have the same biological function. Such mutant proteins can comprise one or more amimo acid deletions, substitutions and/or additions compared to the protein encoded by the sequence mentioned below. Preferably, the mutant proteins still have at least 50%, more preferably at least 70%, even more preferably more than 90% amino acid homology with the sequence given hereinbelow.

The term protein also encompasses fragments of the protein encoded by the chimeric gene of the invention. Such fragments preferably still show the biological activity of the full protein. Preferably, such proteins comprise at least 30%, more preferably at least 50% of the amino acid sequence of the full protein. Also, two or more fragments of the full protein encoded by the chimeric gene of the invention may be combined to form a single protein.

The invention also relates to a nucleotide sequence and to a protein useful for pharmacological purposes, in particular for the prevention and/or treatment of Leishmaniosis, in particular canine Leishmaniosis, having the DNA (SEQ ID NO:11) and amino acid (SEQ ID NO:12) sequence expressed in the vector PQ31. Amino acid residues 1–29 belong to the PQ31 vector and amino acid residues 30–35 belong to both PQ31 and pMal vectors or a mutant or fragment thereof that can be used for generating a protective immune response in a human or animal against Leishmaniosis, and to a pharmaceutical composition for the prevention and treatment, in humans or animals, of *Leishmaniasis*, comprising this protein or a mutant or fragment thereof that can be used for generating a protective immune response in a human or animal against Leishmaniosis. This protein is derived from the insertion of gene PQV in the expression vector pQE31. Here, said chimeric gene preferably encodes a polypeptide generated with a moleuclar weight of 38 kD and an isoelectric point of 7.37.

Probes of the invention are such that they can-most preferably selectively-hybridize with the chimeric gene of the invention or part thereof, in particular under moderate as stringent hybridizing conditions, such as those mentioned above. Preferably, a probe of the invention will be essentially homologous with the nucleotide sequence of the chimeric gene of the invention or a part thereof, i.e. show a homology of more than 80%, preferably more than 90%, more preferably more than 95%.

A skilled person will be able to select suitable probes. Usually, such probes will contain at least 15 bp, preferably more than 24 bp, of the sequence given hereinbelow.

The chimeric gene formed of the DNA sequences that encode the antigenic determinants of four proteins of *L. infantum*, useful for serological diagnosis of canine Leishmaniosis and protein obtained, that the invention proposes, in its own right constitutes an obvious novelty within its field of application, as according to the invention, a synthetic chimeric gene is produced that as it is obtained by assembly, containing the DNA region encoding the antigenic determinants specific to the proteins LiP2a, LiP2b, LiP0 and H2A, thus constructing a protein rich in antigenic determinants. The chimeric gene obtained is expressed in *Escherichia coli* and the product has been analysed with respect to its antigenic properties. The results confirm that this chimeric protein maintains all the antigenic determinants of the parent proteins and that it constitutes a relevant diagnostic element for canine VL, with a sensibility that oscillates between 80% to 93%, and a specificity of between 96% to 100%.

More particularly, the chimeric gene formed by the DNA sequences that encode the antigenic determinants of four proteins of *L. infantum*, useful for the serological diagnostic of canine Leishmaniosis and protein obtained object of the invention, is produced by means of the following stages, namely:

Construction of the chimeric gene. Methodology.
Cloning strategy.
Cloning of DNA sequences that encode antigenic determinants of the histone protein H2A.
Cloning of the sequences that encode rLiP2a-Q and rLiP2b-Q.
Cloning of the sequence rLiPO-Q.
Cloning of the chimeric gene.
Construction of the chimeric gene from the construction of intermediate products.
Cloning of epitopes specific to the *L. infantum* antigens.
Construction of the final product
Construction of the chimeric gene that encodes a polypeptide that contains all the selected antigenic determinants.
Evaluation of the final product.
Serums.
Purification of proteins
Electrophoresis of proteins and immuno-analysis.
Measurements by Fast-ELISA
Evaluation of the final product.
Antigenic properties.
Sensitivity and specificity of the chimeric protein CP in the serum diagnosis of canine VL.

The strategy followed by the cloning of DNA sequences that encode each one of the selected antigenic determinants is the same in all cases, and in a first step, the sequence of interest is amplified by means of a PCR and the use of specific oligonucleotides that contain targets for restriction enzymes at the extremes.

For the cloning step, the amplified product is directed by means of the appropriate restriction enzyme and it is inserted in the corresponding restriction site of the plasmid pUC18.

After sequencing the DNA, the insert is recovered and sub-cloned to the corresponding restriction site of the modified plasmid denominated pMAL-c2. The modification is made by inserting a termination codon downstream of the target HindIII in the polylinker of pMal-c2, denominating the resulting plasmid pMAL-c2*.

Regarding the cloning of the DNA sequence that encodes the antigenic determinants of the histone protein H2A, it should be pointed out that the CDNA of the clone cL71, that encodes the histone H2A of *L. infantum*, is used as a template for the PCR reactions, and for the DNA amplification, that encodes the N-terminal region of the histone H2A, more exactly rLiH2A-Nt-Q, the following oligonucleotides are used: sense 5'-CCTTTAGCTACTCCTCG-CAGCGCCAAG-3' (SEQ ID NO:1) (position 84–104 of the sequence cL71); antisense 5'CCTGGGGGCGCCAGAG-GCACCGATGCG-3' (SEQ ID NO:2) (inverse and complimentary to position 204–224 of the sequence cL71).

The sequences that are included in the oligonucleotides for the cloning and that are not present in the parent sequence cL-71 are marked in boldface type.

The amplified DNA fragment is cloned directly from the restriction site XmnI of pMAI-c2*.

The fragment is sequenced by means of the initiator #1234 malE and the antigenic C-terminal region of histone H2A, in particular rLiH2A-Ct-Q, is amplified with the following oligonucleotides. These are:

Sense, 5'-<u>GAATTC</u>TCCGTAAGGCGGCCGCGCAG-3' (SEQ ID NO:3) (position 276–296 of the sequence cL71).

Antisense, 5'-<u>GAATTC</u>GGGCGCGCTCGGTGTCGCCTTGCC-3' (SEQ ID NO:4) (inverse and complimentary to the positions 456–476 of the plasmid cL71).

A triplet that encodes proline (indicated as GGG after the underlined letters) is included in the anti-sense oligonucleotide, the restriction site EccRI that is included in both oligonucleotides for cloning is indicated by underlining.

Regarding the cloning of the sequences that encode rLiP2a-Q, it should be pointed out that the regions of interest are amplified by PCR from cDNAs encoding LiP2a and LiP2b.

The oligonucleotides that are used for constructing the expression clone LiP2a-Q, are the following.

Sense, 5'-<u>GTCGAC</u>CCCATGCAGTACCTCGCCGCGTAC-3' (SEQ ID NO:5).

Anti-sense, 5'-<u>GTCGAC</u>GGGGCCCATGTCATCATCGGCCTC-3' (SEQ ID NO:6).

It should be pointed out that the SalI restriction sites added to the 5' extremes of the oligonucleotides have been underlined.

When constructing the expression clone LiP2b-Q, the oligonucleotides used were:

Sense, 5'-<u>TCTAGA</u>CCCGCCATGTCGTCGTCTTCCTCGCC-3' (SEQ ID NO:7).

Anti-sense, <u>TCTAGA</u>GGGGCCATGTCGTCGTCGGCCTC-3' (SEQ ID NO:8).

At the 5' extremes of the oligonucleotides the restrictions sites are included for the enzyme XbaI (underlined), and due to the cloning needs, an additional triplet, encoding a proline residue, is included downstream of the restriction site.

Regarding the cloning of the sequence rLiPO-Q, it should be pointed out that the cloning of the DNA sequence of the C-terminal region of the protein PO of *L. infantum* is carried out by amplifying a clone of cDNA called L27 and the following oligonucleotides:

Sense, 5'-<u>CTGCAG</u>CCCGCCGCTGCCGCGCCGGCCGCC-3' (SEQ ID NO:9) (positions 1–24 of the L27 cDNA) and the initiator of the pUC18 sequence (#1211), the amplified DNA is directed by the enzymes PstI+HindIII, with later insertion into the plasmid pMAL-c2.

The resulting clone is denominated PPQI and it should be noted that the restriction site PstI is included in the nucleotide with sense (underlined sequence) and that the restriction target HindIII is present in the cDNA L27.

Regarding the cloning of the chimeric gene, it should be pointed out that the DNA sequences that encode the five antigenic determinants are assembled into a chimeric gene, and this assembly is carried out on the clone pPQI, to which the codifying regions for the antigenic regions LiP2a-Q are added sequentially in the 3' direction (naming The results of cloning pPQ2), LiP2b-Q (clone pPQ3), LiH2a-Ct-Q (clone pPQ4) and LiH2A-Nt-Q (clone pPQ5).

Finally, the insert obtained after the SacI+HindIII digestion of the final clone pPQ5 is inserted into the pQE31 expression plasmid, naming the resulting clone pPQ.

PREFERRED EMBODIMENT OF THE INVENTION

The chimeric gene formed from the DNA sequences that encode the antigenic determinants of four proteins of *L. infantum*, useful for the serological diagnosis of canine Leishmaniosis and the protein obtained that is being proposed are constituted from the construction of intermediate products. In a first instance, cloning of epitopes specific to the antigens of *L. infantum* is carried out, which is configured on the basis of earlier studies on the antigenic properties of four protein antigens of *L. infantum*(LiP2a, PIPO, LiP2b, LiH2a), which allow the existence of B epitopes to be defined for these proteins, and which are specifically recognized by the canine serums of VL.

With a view to improving the antigenic specificity of these antigens with respect to the proteins of *L. infantum*, the specific antigenic determinants are cloned from these proteins. After deleting certain regions of these proteins these can be recognized by serums from animals that are carriers of VL and other different diseases.

By using the specific oligonucleotides and amplification by PCR of regions specific to the genes LiP2a, LiP2b, PO and H2A, several clones are constructed that express the recombinant proteins rLiPO-Ct-Q, rLiP2a-Q, rLiP2b-Q, rLiH2A-Ct-Q and rLiH2A-Nt-Q, just has been detailed in the description of the invention relating to the methodology, where the cloning details are described.

The recombinant proteins used are the following:
rLiPO-Ct-Q, which corresponds to the 30 C-terminal residues of the ribosomal protein LiPO.

rLiP2a-Q and rLiP2b-Q, that are derived from the ribosomal proteins LiP2a and LiP2b respectively.

Two sub-regions of the histone H2A, that correspond to the 47 N-terminus residues (xLiH2A-Nt-Q), and to the 67 C-terminus residues (residues (xLiH2A-Ct-Q).

Each one of the recombinant proteins fused to the maltose binding protein (MBP) is expressed in *E. Coli*, as represented in FIG. 1, and they were purified by affinity chromatography on a amylose column. After the process of purification the electrophoresis was carried out on the recombinant proteins (lanes 1 to 5) in FIG. 3.

With the aim of analysing whether the recombinant proteins were recognised by VL canine serums, a Western blot was incubated, containing the recombinant proteins in a mixture of three VL canine serums. Given that all these proteins are recognised by the serums, it is concluded that the antigenic determinants present in the parent proteins are maintained in the recombinant proteins.

The antigenic properties of the recombinant proteins are compared with the antigenic determinants of the parent antigens by means of a FAST ELISA, testing against a collection of 26 VL canine serums, just as is shown in the section of FIG. 1, and the fact that the serums showed a similar reactivity value, both against the selected antigenic regions and the corresponding complete proteins, demonstrates that no alteration to the antigenic epitope has occurred during the cloning procedure.

Figure 1A:
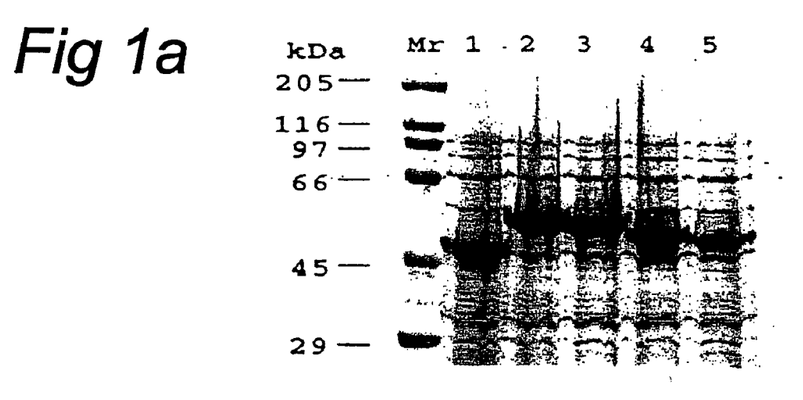
FIGS. 1a–1c show the recombinant proteins fused to the maltose binding protein during the process of purification.
Figure 1B:
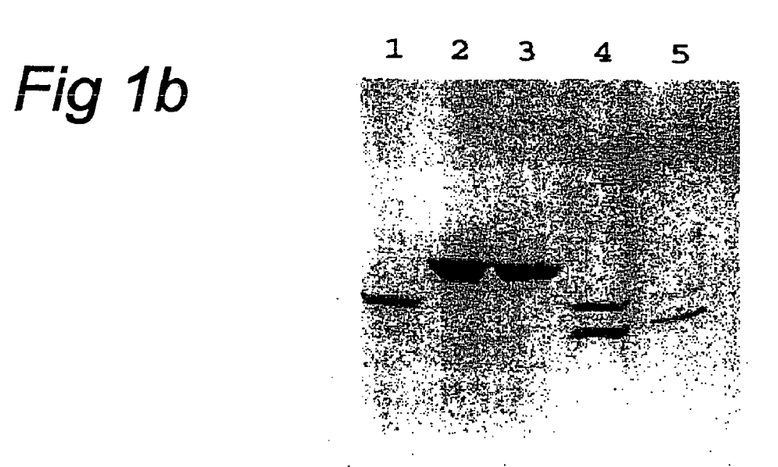
Figure 1C:
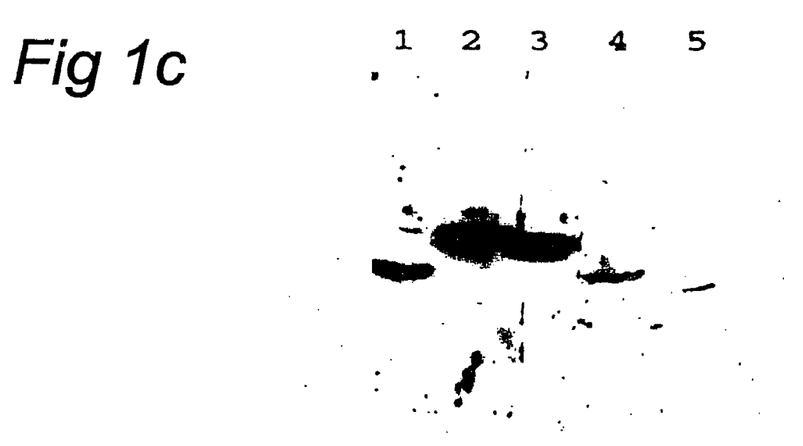
Figure 1D:
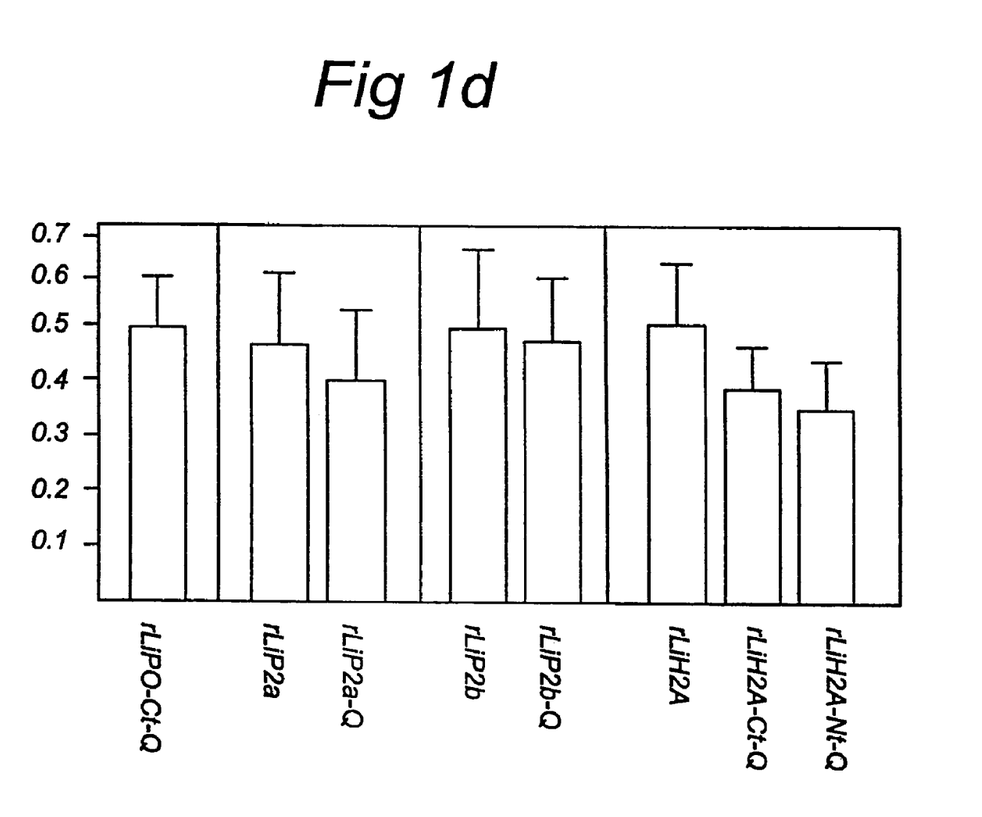
FIG. 1d shows the results of fast ELISA, testing the recombinant proteins against a collection of 26 VL canine serums.
Figure 2:
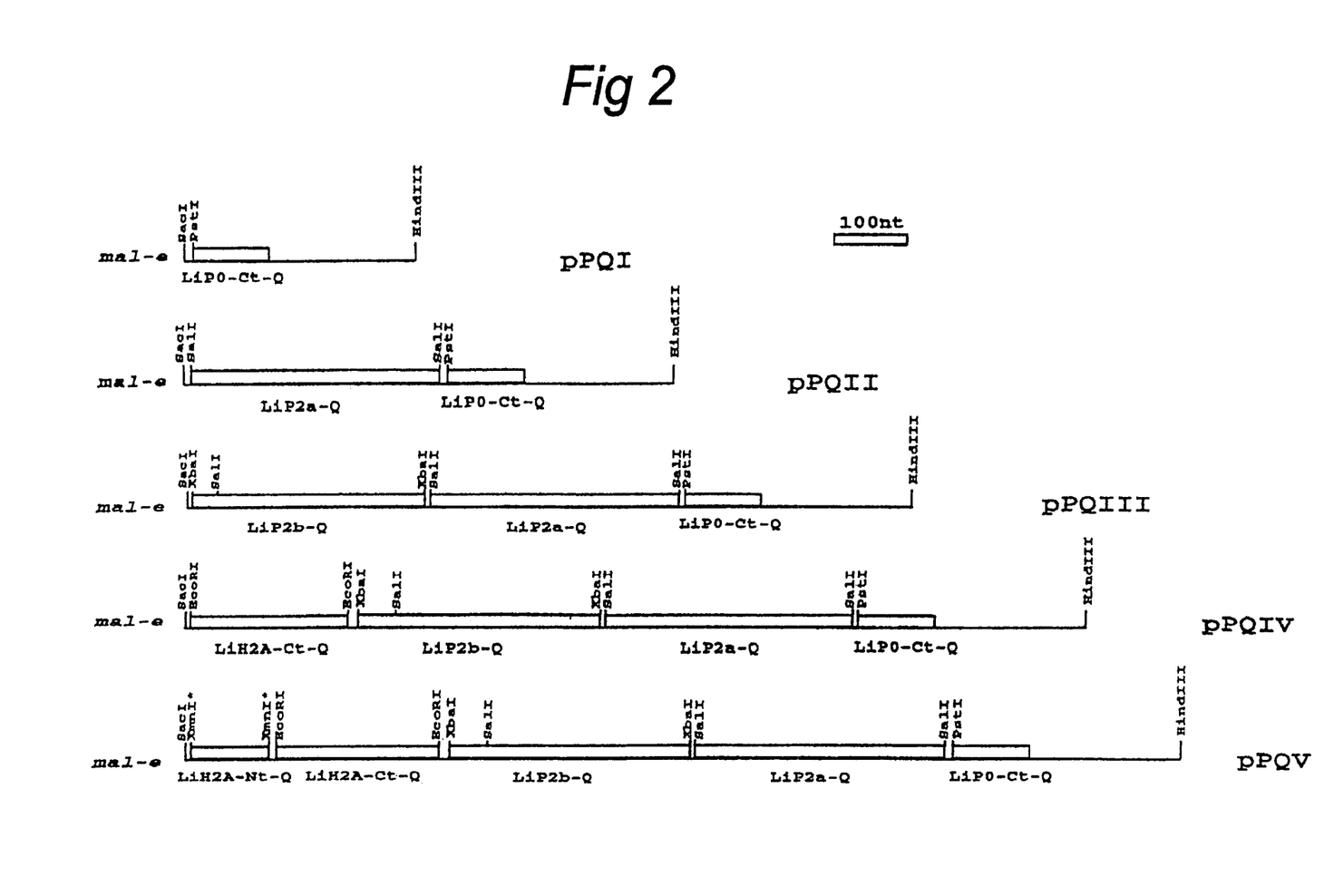
FIG. 2 show schematic representations of the different vectors generated in order to obtain the chimeric gene object of the invention, from which the pertinent protein destined to carry out an accurate diagnostic on animals or human beings that show symptoms of Leishmaniosis will be extracted.

In regard to the construction of the final product, more exactly of the chimeric gene that encodes a polypeptide that contains all the selected antigenic determinants, it should be pointed out that the cloning strategy is indicated following FIG. 2 section A. The intermediate products generated during the process are shown.

A clone that expresses the proteins rLiPO-Ct-Q (pPQI) is used as the initial vector, and the fragments of DNA that encode the proteins rLiPO-Ct-Q, rLiP2a-Q, rLiP2b-Q, rLiH2A-Ct-Q and rLiH2A-Nt-Q are added sequentially using appropriate restriction sites.

Figure 3:
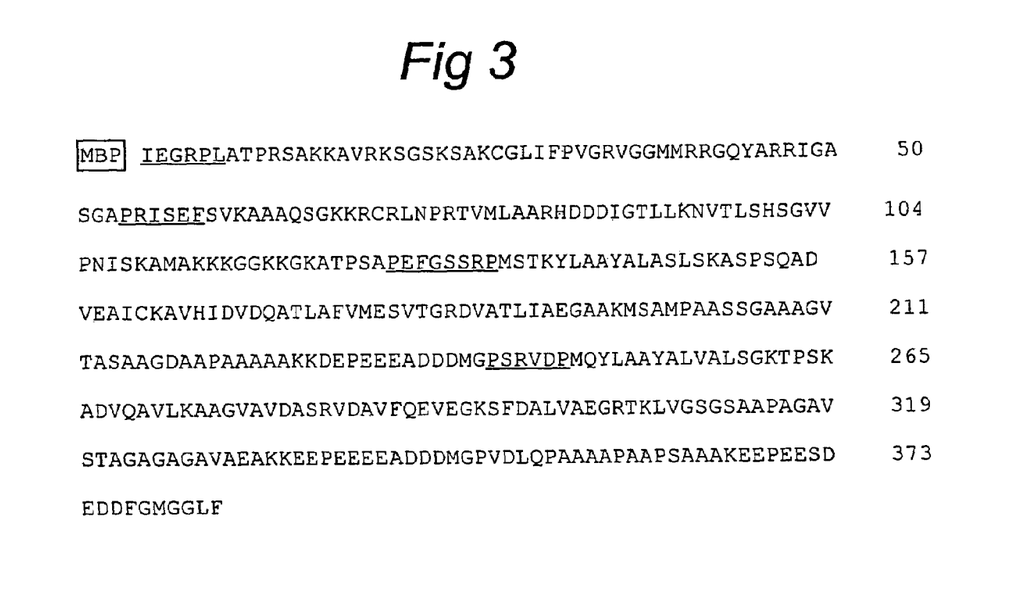
FIG. 3 shows the identification of the protein (SEQ ID NO:10) obtained from the chimeric gene, the preparation of which is represented in FIG. 2. The underlines designate spacer sequences that separate each of the antigenic domains and the maltose binding protein (MBP).
Figure 4A:
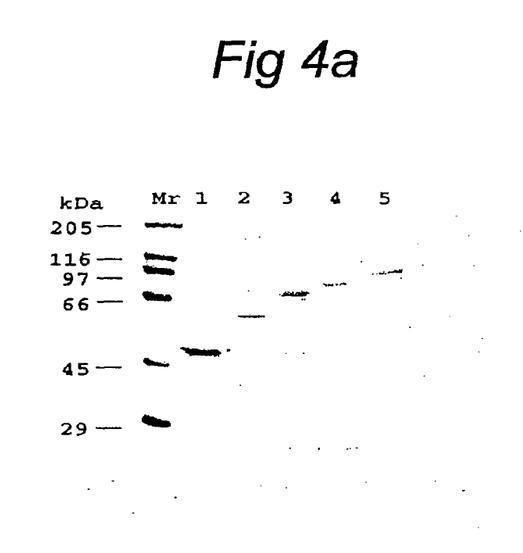
FIGS. 4a–4b are gels showing the expression and recovery of intermediate products in the sequential cloning to obtain recombinant protein pPQV after affinity chomatography on an amylose column.
Figure 4B:
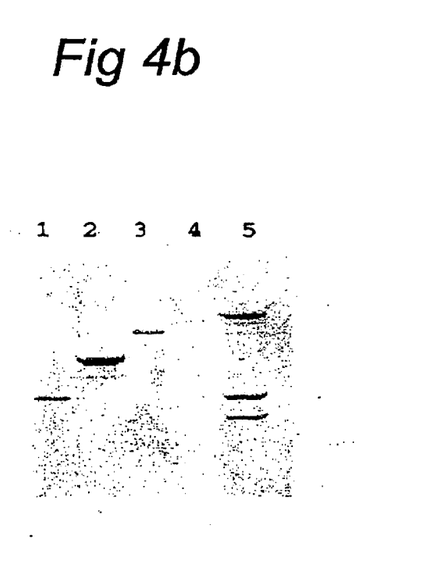
Figure 4C:
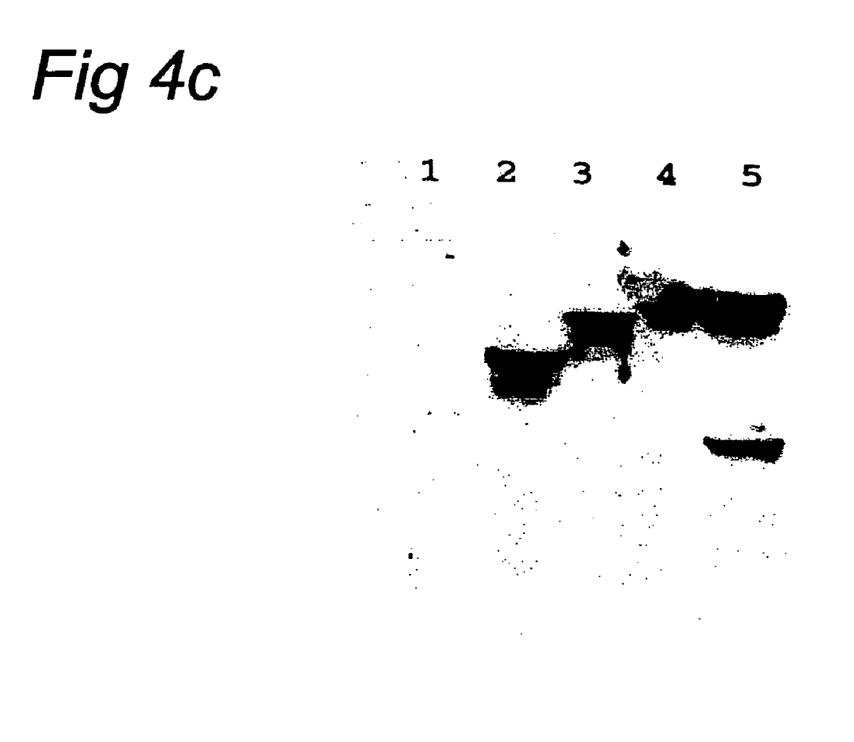
FIGS. 4c–4d are gels showing the level of expression of the protein in bacteria transformed with the pPQ plasmid and the purified proteins.
Figure 4D:
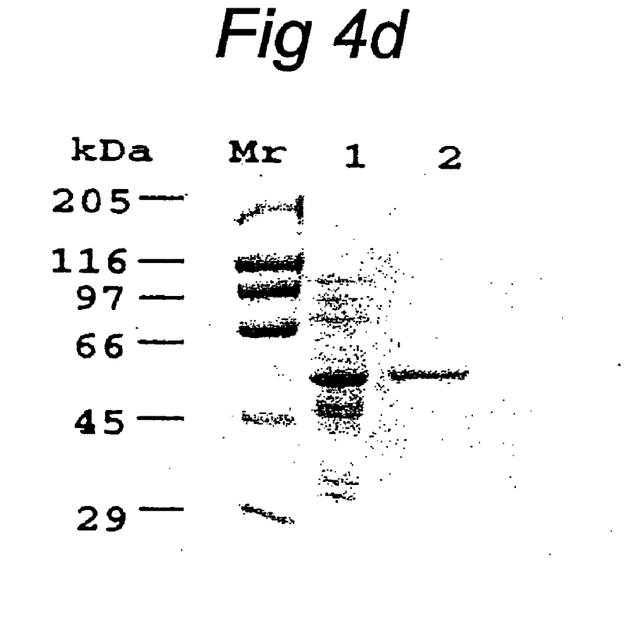
Figure 4E:
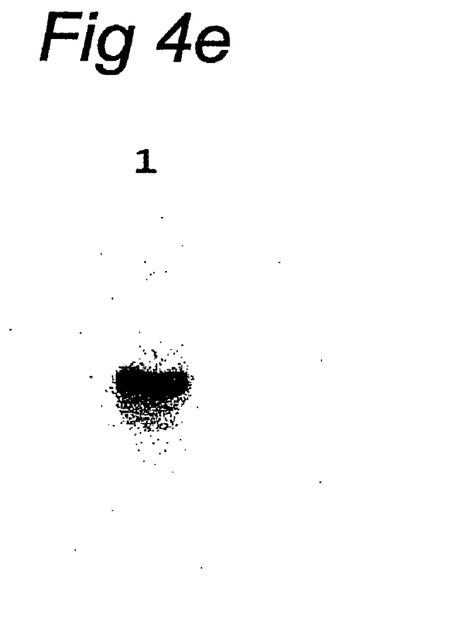
FIG. 4e is a gel showing the recombiant protein pPQV.
Figure 4F:
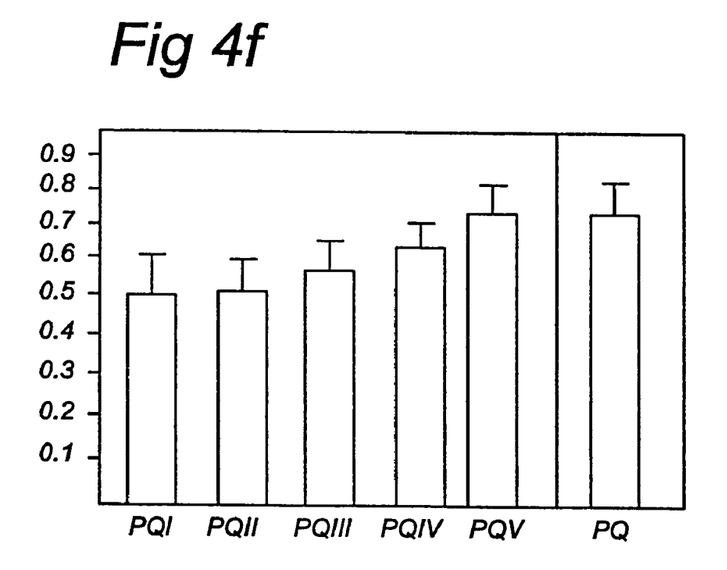
FIG. 4f shows fast-ELISA results of reactivity of a wide variety of VL canine serum against the recombinant proteins.
Figure 5:
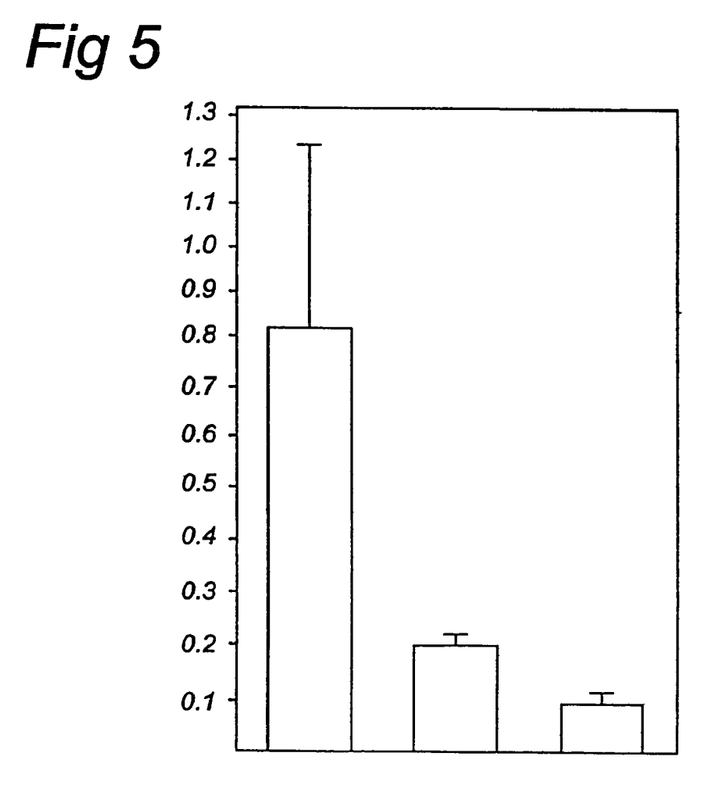
FIG. 5 shows a synthesised graphical representation of the reactivity of a wide variety of canine serums, divided into three groups. The first group contain animals with real infection by *L. infantum*. The second group includes serum obtained from dogs with various clinical symptoms but that are not infected with *Leishmania*, and a third group is made up of fifteen control serums from healthy dogs. This figure demonstrates the value of the invention for carrying out serological diagnosis of VL.

After each cloning step, the correct orientation of each one of the inserts is deduced from the size of the expression products, and finally the complete nucleotide sequence of the final clone pPQV is determined and the amino acid sequence deduced from the sequence represented in FIG. 3.

The polypeptide generated has a molecular mass of 38 kD, with an isoelectric point of 7.37, including spacer sequences encoding proline, underlined in FIG. 3. The aim of doing this is to efficiently separate the antigenic domains and avoid possible tertiary conformations that could interfere with the stability and antigenicity of the final product.

The expression and recovery of each of the intermediate products is shown in FIG. 4, boxes A and B. As was expected, after each addition, the size of the expression product in the vector pMAL gradually increases until reaching a molecular weight of 80 kDa. Included in this are the sizes of the proteins rLiH2A-Ct and rLiH2A-Ct, observing a certain degree of rupture during purification.

The chimeric gene was also cloned in the plasmid pQE, a vector that allows the expression of proteins with a fragment of 6 histidines at the extreme N-terminus.

The resulting clone and the recombinant proteins are denominated pPQ and PQ respectively.

The level of expression of the protein in bacteria transformed with the pPQ plasmid and the purified proteins are shown in FIG. 4, referred to in particular with a D, with the protein PQ, purified by affinity chromatography in denaturising conditions is more stable that the recombinant protein pPQV represented in FIG. 4, in box E.

In order to evaluate the final product a series of materials were used, and obviously some techniques, as is described below.

Serums of VL obtained from dogs of different origins are used. The animals are evaluated clinically and analytically in the pertinent laboratory, generally in a Department of Parasitology, and all the positive serums are assayed for indirect immuno-fluoresence (IIF).

The presence of amastigotes of the parasites of these animals is confirmed by direct observation of the popliteal and pleescapular lymph nodes, and a second group of 33 serums of VL originating from other regions, were given a positive diagnosis in the ELISA against total protein extracts of the parasite and/or by IIF.

The serums of dogs affected by different diseases that were not VL are obtained from different origins. Within this group serums from the following infections are found:

*Mesocestoides* spp.
*Dyphylidium caninum*
*Uncinaria stenocephala*
*Toxocara canis*
*Dipetalonema dranunculoides*
*Demodex canis*
*Babesia canis*
*Ehrlichia cannis*
*Ricketsia ricketsiae.*

The rest of the serums were obtained from dogs that exhibited various clinical symptoms that were not related to any infective process, and the serum controls were obtained from fifteen carefully controlled healthy animals.

Purification of the recombinant proteins expressed by the clones pMA1-c2 is carried out by affinity chromatography on amylose columns, and the purification of the recombinant protein expressed by the clone pPQ was performed on Ni-NTA resin columns in denaturising conditions (Qiagen).

For analysing the proteins electrophoresis on 10% polyacrimide gels in the presence of SDS was carried out under standard conditions. Immunological analysis of the proteins separated by electrophoresis was carried out on nitrocellulose membranes to which the proteins had been transferred. The transferred proteins were blocked with dried 5% skimmed milk in a PBS buffer with 0.5% Tween 20.

The filters were sequentially brought into contact with primary and secondary anti-serum in blocking solutions and an immuno-conjugate labelled with peroxidase was used as second antibody, visualising the specific binding by means of an ECL system.

The Fast-ELISA was used instead of the classic ELISA, and the sensitisation of the antigen was carried out for 12 hours at room temperature.

The plates were sensitised with 100 ιl of antigen whose concentration in all cases was 2 ιg/ml.

After sensitising the wells the plates were incubated for 1 hour with blocking solution (0.5% powdered skimmed milk dissolved in PBS—0.5% Tween 20 and the serums were diluted three hundred fold in blocking solution).

The wells were incubated with serum for 2 hours at room temperature, and after exposure to the antibody the wells were washed with PBS-Tween 20.

Antibodies labelled with peroxidase were used as second antibodies at a dilution of 1:2000 and the colour of the reaction was developed using the substrate ortho-phenylenediamine, measuring the absorption at 450 nm.

In regard to evaluation of the final product, it should be pointed out that the antigenic properties were determined by means of the pertinent study of the reactivity of the VL canine serums against the chimeric protein and against each one of the intermediate products in a "Western blot" assay. All the intermediate products maintained their antigenicity as well as did the final pPQV product, throughout the whole of the cloning process.

It should also be pointed out that the recombinant protein expressed by the pPQ plasmid was recognised by the VL serums. With a view to analysing with greater precision the antigenic properties of the chimeric protein and the intermediate products, an analysis of the reactivity of a wide variety of VL canine serums was performed by means of a fast-ELISA against the recombinant proteins, as is shown in the section F of FIG. 4. It can be highlighted that the absorption values and the sensitivity of the different intermediate products of cloning increases after each addition stop. It should also be pointed out that the protein pQI is recognised by most of the VL serums and the protein PQII equally by most of the serums. This proportion is greater for the protein PQIII, and the proteins PQIV, PQV and PQ are recognised by practically all the serums.

According to what has been discussed above, the percentage of recognition shown by the serums was similar both in the case of assaying the chimeric proteins PQV and PQ, and of assaying a mixture of recombinant proteins rLiPO-Ct-Q, rLiP2a, rLiP2b and rLiH2A. It was seen that the antigenic properties of each one of the 5 selected antigenic regions are present in the PQ expression product, and therefore this product can be used for diagnosis instead of a mixture of the antigens expressed individually.

With a view to determining whether the chimeric protein can be used for canine VL serum diagnosis, and according to the pertinent analysis of a wide variety of canine serums against this protein, bearing in mind that according to the clinical characteristics of the animals, the canine serums have been classified into three groups. A first group consisted of serum of dogs with a real *L. infantum* infection. A second group was composed of serums of dogs that had various clinical symptoms without being infected with *Leishmania*, including dogs infected with parasites different to *Leishmania* incorporated into this group. The rest of the serums originated from dogs that exhibit clinical symptoms that could be confused with those observed during Leishmaniosis.

The third group was made up of control serums, originated from serums of healthy dogs.

In FIG. 5 the average values of reactivity are shown for each group of serums, the reactivity of the VL serums reaching an average reactivity value of 0.8 (S.D.=0.4).

Within this group the reactivity of 12 serums is less than 0.35, while the reactivity of 10 serums reaches values of between 0.35 and 0.5. It is observed that the reactivity over 23 serums varies between 0.5 and 1.0, with 14 serums showing a reactivity greater than 1.0.

The average absorption value of the serums of the second group, that is to say, the group in which animals infected with *Leishmania* parasites and parasites different to *Leishmania* parasites, is 0.2 (S.D.=0.05) and the reactivity of the control serums, that is to say, the third group, is 0.1 (S.D.=0.003).

The data presented above indicate that the chimeric protein PQ in the FAST ELISA has a sensitivity of 80% for the VL diagnosis, if the cut-off value is defined as the average reactivity value of the serums of group 2 plus three S.D.’s (that is to say 0.35).

The sensitivity of the assayed group reaches 93%, if the cut-off value is defined by the reactivity values of the control group, and the data indicate that the protein CP has a specificity of 96% for the VL diagnosis, when the cut-off value is defined by the aforementioned serums of group 2, and only two serums from group 2 showed reactivity between 0.35 and 0.40. 100% specificity in the assay was reached when the reactivity values of healthy dogs were considered.

The process to be used is the following:

1.—The microtitre plates are covered with antigens by incubating 100 ίl of a solution that contains 1 ί/ml of antigen dissolved in a buffer PBS—-0.5% Tween 20–5% skimmed milk (Buffer A).

The incubation is performed for 12 hours at room temperature, and then the plates are washed three times with the same buffer containing no antigen. The dry antigenated plates could be maintained at room temperature.

2.—A first incubation of the wells was carried out with the serum of animal at a dilution of 1/200 in buffer A. The incubation lasts for 1 hour.

3.—The wells are washed with buffer A, as described in point 1, three times with a wash flask.

4.—They are incubated with a second antibody (IgG labelled with peroxide) diluted 1:2000 in buffer A, carrying out the incubation for 1 hour.

5.—The wells are washed once again with buffer A three times, as was indicated in the third section, that is to say with a wash flask.

6.—The reactivity is revealed using the substrate orthophenylenediamine and the absorption measured at 450 nm.

The protein used for the diagnosis extracted from the chimeric gene is identified as (SEQ ID NO:10).

It is not considered necessary to extend this description in order that someone skilled in the art can understand the scope of the invention and the advantages that it confers.

The materials, form, size and disposition of the elements are susceptible to change, provided it does not suppose a change in the essence of the invention.

The terms in which this disclosure has been written should always be considered as broad in nature and not limiting.

What is claimed is:

1. A pharmaceutical composition, comprising a chimeric polypeptide and a carrier, said chimeric polypeptide, which contains at least one antigenic determinant, recognized by serum from dogs with visceral Leishmaniosis, from each of the LiP2a, LiP2b, LiH2a, and LiPO proteins from *Leishmania infantum*, being encoded by a polynucleotide.

2. A method for inhibiting or treating visceral Leishmaniosis, comprising administering the pharmaceutical composition of claim 1 to a human or animal subject in need thereof.

* * * * *